(12) United States Patent
Govari

(10) Patent No.: US 9,131,981 B2
(45) Date of Patent: Sep. 15, 2015

(54) CATHETER WITH HELICAL ELECTRODE

(71) Applicant: BIOSENSE WEBSTER (ISRAEL), LTD., Yokneam (IL)

(72) Inventor: Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 0 days.

(21) Appl. No.: 13/760,335

(22) Filed: Feb. 6, 2013

(65) Prior Publication Data

US 2013/0150847 A1 Jun. 13, 2013

Related U.S. Application Data

(62) Division of application No. 12/639,096, filed on Dec. 16, 2009.

(51) Int. Cl.
*A61B 18/18* (2006.01)
*A61B 18/14* (2006.01)
*A61B 17/32* (2006.01)
*A61B 18/00* (2006.01)

(52) U.S. Cl.
CPC ..... *A61B 18/1492* (2013.01); *A61B 17/320068* (2013.01); *A61B 18/1815* (2013.01); *A61B 2018/00011* (2013.01); *A61B 2018/1407* (2013.01); *A61B 2018/1435* (2013.01); *A61B 2018/1861* (2013.01); *A61B 2218/002* (2013.01)

(58) Field of Classification Search
CPC ............... A61B 18/1492; A61B 2018/00011; A61B 2018/00065; A61B 2018/00577; A61B 2018/1435

USPC .......... 606/32, 41, 49; 29/874, 876, 877, 884, 29/837

See application file for complete search history.

(56) References Cited

U.S. PATENT DOCUMENTS

| | | |
|---|---|---|
| 3,971,364 A | 7/1976 | Fletcher et al. |
| 4,488,561 A | 12/1984 | Doring |
| 4,764,114 A | 8/1988 | Jeffcoat et al. |
| 4,856,993 A | 8/1989 | Maness et al. |
| 4,917,102 A | 4/1990 | Miller et al. |
| 4,917,104 A | 4/1990 | Rebell |
| 5,263,493 A | 11/1993 | Avitall |
| 5,334,193 A * | 8/1994 | Nardella .................. 606/41 |
| 5,368,564 A | 11/1994 | Savage |
| 5,391,199 A | 2/1995 | Ben-Haim |

(Continued)

FOREIGN PATENT DOCUMENTS

| | | |
|---|---|---|
| DE | 19750441 A | 6/1999 |
| EP | 856292 A1 | 8/1998 |

(Continued)

OTHER PUBLICATIONS

Biter, W.J. et al., "Magnetic Wire Strain Sensor", 33rd International Sampe Technical Conference, Nov. 2001, vol. 33, pp. 12-23, Seattle, WA.

(Continued)

*Primary Examiner* — Joseph Stoklosa
*Assistant Examiner* — Jocelyn D Ram

(57) ABSTRACT

An invasive probe includes an insertion tube containing a lumen for providing an irrigation fluid and comprising a distal portion having a plurality of perforations therethrough providing fluid communication between the lumen and an outer surface of the insertion tube. At least one helical electrode is fitted over the distal portion of the insertion tube.

10 Claims, 4 Drawing Sheets

(56) References Cited

U.S. PATENT DOCUMENTS

| | | |
|---|---|---|
| 5,487,757 A | 1/1996 | Truckai et al. |
| 5,499,542 A | 3/1996 | Morlan |
| 5,558,091 A | 9/1996 | Acker et al. |
| 5,563,354 A | 10/1996 | Kropp |
| 5,643,197 A * | 7/1997 | Brucker et al. ............ 604/20 |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,718,701 A | 2/1998 | Shai et al. |
| 5,730,127 A | 3/1998 | Avitall |
| 5,769,843 A | 6/1998 | Abela et al. |
| 5,820,591 A | 10/1998 | Thompson et al. |
| 5,826,576 A | 10/1998 | West |
| 5,836,894 A | 11/1998 | Sarvazyan |
| 5,860,920 A | 1/1999 | McGee et al. |
| 5,860,974 A | 1/1999 | Abele |
| 5,865,815 A | 2/1999 | Tihon |
| 5,871,523 A | 2/1999 | Fleischman et al. |
| 5,876,398 A * | 3/1999 | Mulier et al. ............ 606/41 |
| 5,902,248 A | 5/1999 | Millar et al. |
| 5,913,854 A * | 6/1999 | Maguire et al. ............ 606/41 |
| 5,916,147 A | 6/1999 | Boury |
| 5,938,694 A | 8/1999 | Jaraczewski et al. |
| 5,944,022 A | 8/1999 | Nardella et al. |
| 5,964,757 A | 10/1999 | Ponzi |
| 5,974,320 A | 10/1999 | Ward et al. |
| 5,983,126 A | 11/1999 | Wittkampf |
| 6,002,955 A | 12/1999 | Willems et al. |
| 6,048,329 A | 4/2000 | Thompson et al. |
| 6,063,022 A | 5/2000 | Ben-Haim |
| 6,064,902 A | 5/2000 | Haissaguerre et al. |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,267,781 B1 | 7/2001 | Tu |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,335,617 B1 | 1/2002 | Osadchy et al. |
| 6,371,955 B1 | 4/2002 | Fuimaono et al. |
| 6,436,059 B1 | 8/2002 | Zanelli |
| 6,456,864 B1 | 9/2002 | Swanson et al. |
| 6,468,260 B1 | 10/2002 | Bumbalough et al. |
| 6,484,118 B1 | 11/2002 | Govari |
| 6,500,167 B1 | 12/2002 | Webster, Jr. |
| 6,522,930 B1 * | 2/2003 | Schaer et al. ............ 607/101 |
| 6,522,933 B2 | 2/2003 | Nguyen |
| 6,551,302 B1 | 4/2003 | Rosinko et al. |
| 6,574,492 B1 | 6/2003 | Ben-Haim et al. |
| 6,584,856 B1 | 7/2003 | Biter et al. |
| 6,592,581 B2 | 7/2003 | Bowe |
| 6,602,242 B1 | 8/2003 | Fung et al. |
| 6,612,992 B1 | 9/2003 | Hossack et al. |
| 6,618,612 B1 | 9/2003 | Acker et al. |
| 6,669,692 B1 * | 12/2003 | Nelson et al. ............ 606/41 |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,712,815 B2 * | 3/2004 | Sampson et al. ............ 606/41 |
| 6,723,094 B1 | 4/2004 | Desinger |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,908,464 B2 | 6/2005 | Jenkins et al. |
| 6,911,019 B2 | 6/2005 | Mulier et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,008,401 B2 | 3/2006 | Thompson et al. |
| 7,008,418 B2 | 3/2006 | Hall et al. |
| 7,077,823 B2 | 7/2006 | McDaniel |
| 7,156,816 B2 | 1/2007 | Schwartz et al. |
| 7,235,070 B2 | 6/2007 | Vanney |
| 7,285,119 B2 | 10/2007 | Stewart et al. |
| 7,306,593 B2 | 12/2007 | Keidar et al. |
| 7,311,704 B2 | 12/2007 | Paul et al. |
| 7,397,364 B2 | 7/2008 | Govari |
| 7,419,489 B2 * | 9/2008 | Vanney et al. ............ 606/41 |
| 7,481,774 B2 | 1/2009 | Brockway et al. |
| 7,517,349 B2 | 4/2009 | Truckai et al. |
| 7,536,218 B2 | 5/2009 | Govari et al. |
| 7,604,605 B2 | 10/2009 | Zvuloni |
| 7,681,432 B2 | 3/2010 | Hay et al. |
| 7,686,767 B2 | 3/2010 | Maschke |
| 7,815,635 B2 | 10/2010 | Wittkampf |
| 8,066,702 B2 * | 11/2011 | Rittman et al. ............ 606/41 |
| 8,083,691 B2 | 12/2011 | Goldenberg et al. |
| 8,628,526 B2 * | 1/2014 | Laufer et al. ............ 606/41 |
| 2001/0007070 A1 * | 7/2001 | Stewart et al. ............ 606/41 |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0022839 A1 | 2/2002 | Stewart et al. |
| 2002/0065455 A1 | 5/2002 | Ben-Haim et al. |
| 2002/0068866 A1 | 6/2002 | Zikorus et al. |
| 2002/0165461 A1 | 11/2002 | Hayzelden et al. |
| 2002/0193781 A1 | 12/2002 | Loeb |
| 2003/0060822 A1 * | 3/2003 | Schaer et al. ............ 606/41 |
| 2003/0105453 A1 | 6/2003 | Stewart et al. |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0216722 A1 * | 11/2003 | Swanson ............ 606/32 |
| 2004/0049255 A1 | 3/2004 | Jain et al. |
| 2004/0064024 A1 | 4/2004 | Sommer |
| 2004/0068178 A1 | 4/2004 | Govari |
| 2004/0082948 A1 | 4/2004 | Stewart et al. |
| 2004/0097806 A1 | 5/2004 | Hunter et al. |
| 2004/0102769 A1 | 5/2004 | Schwartz et al. |
| 2004/0143175 A1 | 7/2004 | Coleman et al. |
| 2004/0147920 A1 | 7/2004 | Keidar |
| 2004/0152974 A1 | 8/2004 | Solomon et al. |
| 2004/0158141 A1 | 8/2004 | Scheib |
| 2004/0244464 A1 | 12/2004 | Hajdukiewicz et al. |
| 2004/0254458 A1 | 12/2004 | Govari |
| 2005/0004565 A1 | 1/2005 | Vanney |
| 2005/0010095 A1 | 1/2005 | Stewart et al. |
| 2005/0033135 A1 | 2/2005 | Govari |
| 2005/0070894 A1 | 3/2005 | McClurken |
| 2005/0080429 A1 | 4/2005 | Freyman et al. |
| 2005/0187544 A1 | 8/2005 | Swanson et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0020264 A1 * | 1/2006 | Crowley et al. ............ 606/41 |
| 2006/0106295 A1 | 5/2006 | Jais et al. |
| 2006/0173480 A1 | 8/2006 | Zhang |
| 2006/0200049 A1 | 9/2006 | Leo et al. |
| 2006/0235381 A1 * | 10/2006 | Whayne et al. ............ 606/49 |
| 2006/0247618 A1 | 11/2006 | Kaplan et al. |
| 2006/0253116 A1 | 11/2006 | Avitall et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |

(56) References Cited

U.S. PATENT DOCUMENTS

| | | |
|---|---|---|
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0097394 A1 | 4/2008 | Lampropoulos et al. |
| 2008/0161774 A1 | 7/2008 | Hastings et al. |
| 2008/0161795 A1 | 7/2008 | Wang et al. |
| 2008/0183075 A1 | 7/2008 | Govari et al. |
| 2008/0249522 A1 | 10/2008 | Pappone et al. |
| 2008/0255540 A1 | 10/2008 | Selkee |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0254083 A1 | 10/2009 | Wallace et al. |
| 2009/0287118 A1 | 11/2009 | Malek |
| 2009/0306650 A1 | 12/2009 | Govari et al. |
| 2010/0030209 A1 | 2/2010 | Govari et al. |
| 2010/0063478 A1 | 3/2010 | Selkee |
| 2010/0137845 A1 | 6/2010 | Ramstein et al. |
| 2010/0145423 A1* | 6/2010 | Seifert ............ 607/116 |
| 2010/0152574 A1 | 6/2010 | Erdman et al. |
| 2010/0168548 A1 | 7/2010 | Govari et al. |
| 2010/0168620 A1 | 7/2010 | Klimovitch et al. |
| 2010/0168918 A1 | 7/2010 | Zhao et al. |
| 2010/0222859 A1 | 9/2010 | Govari et al. |
| 2011/0034989 A1 | 2/2011 | Al-Marashi et al. |
| 2011/0054287 A1 | 3/2011 | Schultz |
| 2011/0054446 A1 | 3/2011 | Schultz |
| 2011/0130648 A1 | 6/2011 | Beeckler et al. |
| 2011/0144639 A1 | 6/2011 | Govari et al. |
| 2011/0160719 A1 | 6/2011 | Govari et al. |
| 2011/0184406 A1 | 7/2011 | Selkee |
| 2012/0053403 A1* | 3/2012 | Ducharme et al. ............ 600/104 |
| 2012/0143088 A1 | 6/2012 | Schultz |
| 2012/0172703 A1 | 7/2012 | Esguerra et al. |
| 2013/0006238 A1 | 1/2013 | Ditter et al. |

FOREIGN PATENT DOCUMENTS

| | | |
|---|---|---|
| EP | 928601 A | 7/1999 |
| EP | 1042990 A | 10/2000 |
| EP | 1181896 A1 | 2/2002 |
| EP | 1502555 A | 2/2005 |
| EP | 1586281 A | 10/2005 |
| EP | 1690564 A | 8/2006 |
| EP | 1743575 A | 1/2007 |
| EP | 1820464 A | 8/2007 |
| EP | 1897581 A | 3/2008 |
| EP | 2000789 A | 12/2008 |
| EP | 2047797 A | 4/2009 |
| EP | 2127604 A | 12/2009 |
| EP | 2130508 A | 12/2009 |
| EP | 2229904 A | 9/2010 |
| EP | 2289403 A | 3/2011 |
| EP | 2289408 A | 3/2011 |
| EP | 2338411 A | 6/2011 |
| EP | 2338412 A | 6/2011 |
| JP | 2005345215 A | 12/2005 |
| JP | 2006064465 A | 3/2006 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 99/56812 A | 11/1999 |
| WO | WO 03/020139 A | 3/2003 |
| WO | WO 2006/003216 A | 1/2006 |
| WO | WO 2006/029563 A | 3/2006 |
| WO | WO 2006/086152 A | 8/2006 |
| WO | WO 2006/092563 A | 9/2006 |
| WO | WO 2007/025230 A | 3/2007 |
| WO | WO 2007/050960 A | 5/2007 |
| WO | WO 2007/067938 A | 6/2007 |
| WO | WO 2007/082216 A | 7/2007 |
| WO | WO 2007/098494 A | 8/2007 |
| WO | WO 2007/111182 A | 10/2007 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |

OTHER PUBLICATIONS

Biter, W.J. et al., "Magnetic Wire for Monitoring Strain in Composites", *Sensors*, Jun. 2001, www.sensormag.com, pp. 110-114.

Okumura, Y. et al., "A Systematic Analysis of In Vivo Contact Forces on Virtual Catheter Tip-Tissue Surface Contact During Cardiac Mapping and Intervention", *J. of Cardiovasc Electrophysiol*, vol. 19, pp. 632-640, Jun. 2008.

* cited by examiner

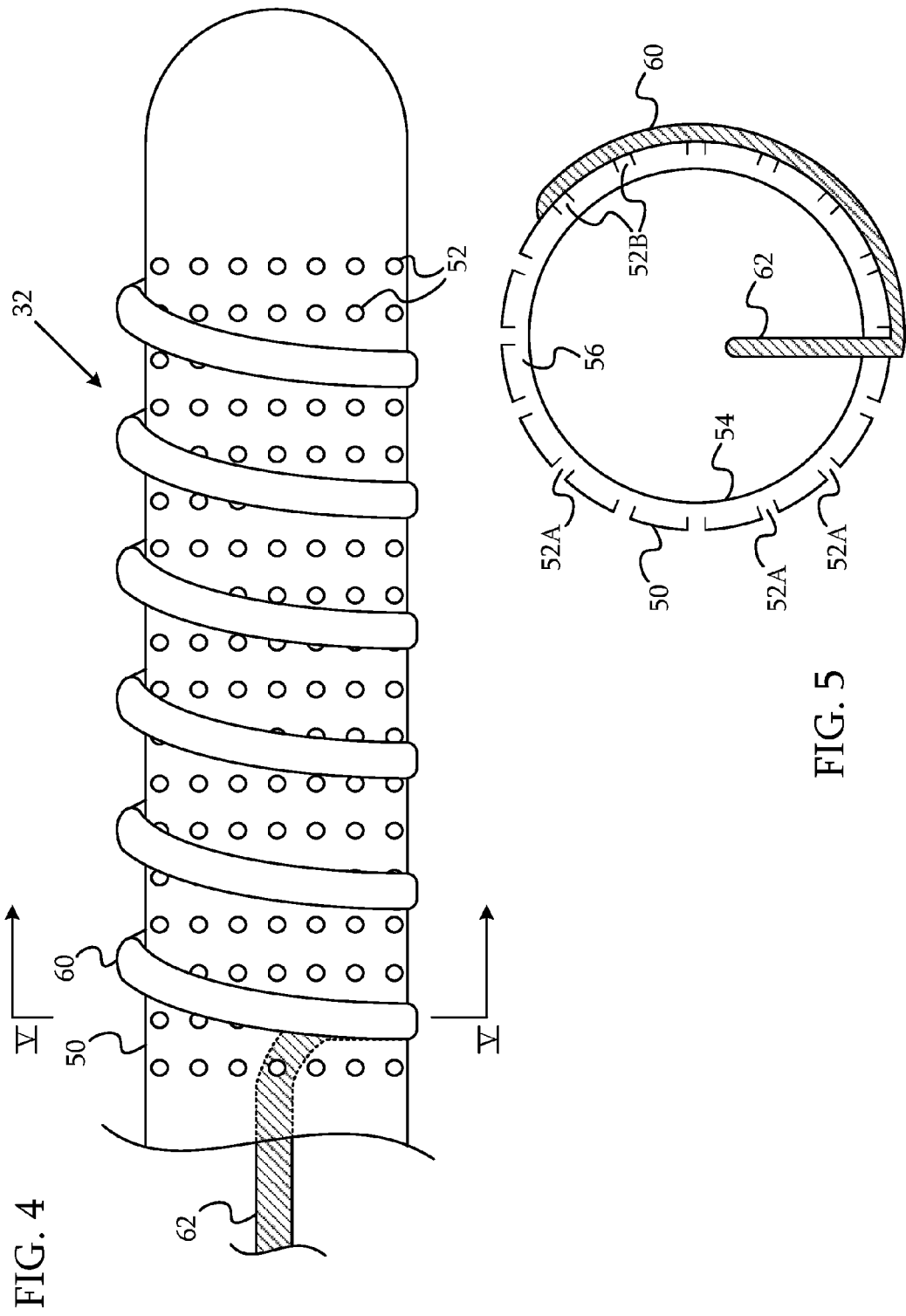

CATHETER WITH HELICAL ELECTRODE

This application is a divisional of U.S. application Ser. No. 12/639,096 filed Dec. 16, 2009, the complete disclosure of which is hereby incorporated herein by reference for all purposes.

FIELD OF THE INVENTION

The present invention relates generally to medical devices, and specifically to cooling of tissue contacted by an invasive probe within the body.

BACKGROUND OF THE INVENTION

In some medical procedures, energy is imparted to body tissue locally, in a concentrated dose, and it is desirable to cool the treatment area in order to reduce collateral tissue damage.

For example, cardiac ablation therapy is used to treat arrhythmias by heating tissue with radio-frequency (RF) electrical energy to create non-conducting lesions in the myocardium. It has been found that cooling the area of the ablation site reduces tissue charring and thrombus formation. For this purpose, Biosense Webster Inc. (Diamond Bar, Calif.) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

SUMMARY

Embodiments of the present invention that are described hereinbelow provide irrigated probes for invasive medical procedures, such as irrigated catheters for use in RF ablation, as well as efficient methods for manufacturing such probes.

There is therefore provided, in accordance with an embodiment of the present invention, an invasive probe, including an insertion tube containing a lumen for providing an irrigation fluid and including a distal portion having a plurality of perforations therethrough providing fluid communication between the lumen and an outer surface of the insertion tube. At least one helical electrode is fitted over the distal portion of the insertion tube.

Typically, the probe includes one or more wires that pass through the tube and are electrically coupled to the at least one helical electrode. Additionally or alternatively, the at least one helical electrode covers some of the perforations.

In one embodiment, the at least one helical electrode includes multiple helical electrodes, which are distributed along the distal portion.

In a disclosed embodiment, the insertion tube is configured for insertion through a blood vessel into a chamber of a heart of a subject, so as to bring the at least one helical electrode into contact with endocardial tissue in the heart.

Typically, the plurality of the perforations includes at least eight perforations, and possibly at least fifty perforations. The perforations typically have a diameter less than 0.5 mm, and possibly less than 0.2 mm. The perforations may have respective sizes that vary depending on respective longitudinal locations of the perforations.

In one embodiment, the at least one helical electrode includes a wire coil helically wound about the distal portion of the insertion tube. In another embodiment, the at least one helical electrode includes a tube cut out along a spiral pattern.

There is also provided, in accordance with an embodiment of the present invention, medical apparatus, including a probe, for insertion into a body of a subject. The probe includes an insertion tube containing a lumen and including a distal portion having a plurality of perforations therethrough providing fluid communication between the lumen and an outer surface of the insertion tube, with at least one helical electrode fitted over the distal portion of the insertion tube and configured to contact tissue in the body. An energy generator is coupled to the probe so as to supply electrical energy to the at least one helical electrode. An irrigation pump is coupled to the lumen so as to supply an irrigation fluid via the lumen and the perforations to the tissue.

In a disclosed embodiment, the energy generator is coupled to supply electrical energy to the at least one helical electrode in order to ablate the tissue. For example, the probe may be configured for insertion through a blood vessel into a heart of the subject for ablation of myocardial tissue in the heart.

There is additionally provided, in accordance with an embodiment of the present invention, a method for treatment, including inserting a probe into a body of a subject. The probe includes an insertion tube containing a lumen and including a distal portion having a plurality of perforations therethrough providing fluid communication between the lumen and an outer surface of the insertion tube, with at least one helical electrode fitted over the distal portion of the insertion tube. The at least one helical electrode is brought into contact with tissue in the body. Electrical energy is applied through the at least one helical electrode to the tissue, and an irrigation fluid is supplied via the lumen and the perforations to the tissue.

Typically, the fluid is supplied in order to cool the distal portion and the tissue.

There is further provided, in accordance with an embodiment of the present invention, a method for producing a medical device, including creating a plurality of perforations through an outer surface of a distal portion of an insertion tube containing a lumen so as to provide fluid communication between the lumen and an outer surface of the insertion tube. At least one helical electrode, including a conductive material, is slid over the distal portion of the insertion tube. The at least one helical electrode is then affixed to the outer surface of the distal portion of the insertion tube.

The present invention will be more fully understood from the following detailed description of the embodiments thereof, taken together with the drawings in which:

BRIEF DESCRIPTION OF THE DRAWINGS

FIG. 4 is a schematic side view of the distal portion of a perforated catheter onto which a coil electrode has been fitted, in accordance with an embodiment of the present invention;

FIG. 5 is a schematic, cross-sectional view of the catheter of FIG. 4, taken along a line V-V.

DETAILED DESCRIPTION OF EMBODIMENTS

In RF electrical ablation procedures, as noted earlier, irrigating the area of the ablation site reduces tissue charring, thrombus formation, and adhesion between the ablation electrode and the tissue. Methods and devices for irrigation to date have required that the electrode itself be perforated so that irrigation fluid can pass out of the catheter through the perforations into the treatment area. A perforated electrode of this type and methods for producing the perforations are described, for example, in U.S. patent application Ser. No. 12/173,150, filed Jul. 15, 2008, which is assigned to the assignee of the present patent application and whose disclosure is incorporated herein by reference. Creating the perforations is time-consuming and costly, however, and may weaken the electrode structure.

Embodiments of the present invention that are described hereinbelow provide a simple, inexpensive method for producing ring electrodes with irrigation. An invasive probe, such as a catheter, is produced with multiple perforations through its outer wall in the area in which a ring electrode is to be placed. The perforations communicate with a lumen inside the probe, which conveys irrigation fluid to the perforations. A conductive coil electrode, typically having the form and resilience of a helical spring, is fitted over and fixed to the probe at the desired electrode location. This coil electrode is connected to one or more wires running through the probe, which may be used, for example, to provide RF electrical energy to the coil for ablation therapy. Although the placement of the coil electrode will typically cover some of the perforations in the wall of the probe, other perforations, in the gaps between the turns of the coil, remain uncovered. During operation, these open perforations provide irrigation throughout the treatment area.

The design described above and shown in the figures that follow is easy and inexpensive to manufacture. It provides the benefits achieved by a perforated, irrigated electrode, while avoiding the difficulty and costs of actually creating the perforations in the electrode. This sort of electrode structure can be used in creating multiple ring electrodes along the length of a catheter or other structure, such as lasso.

Figure 1:
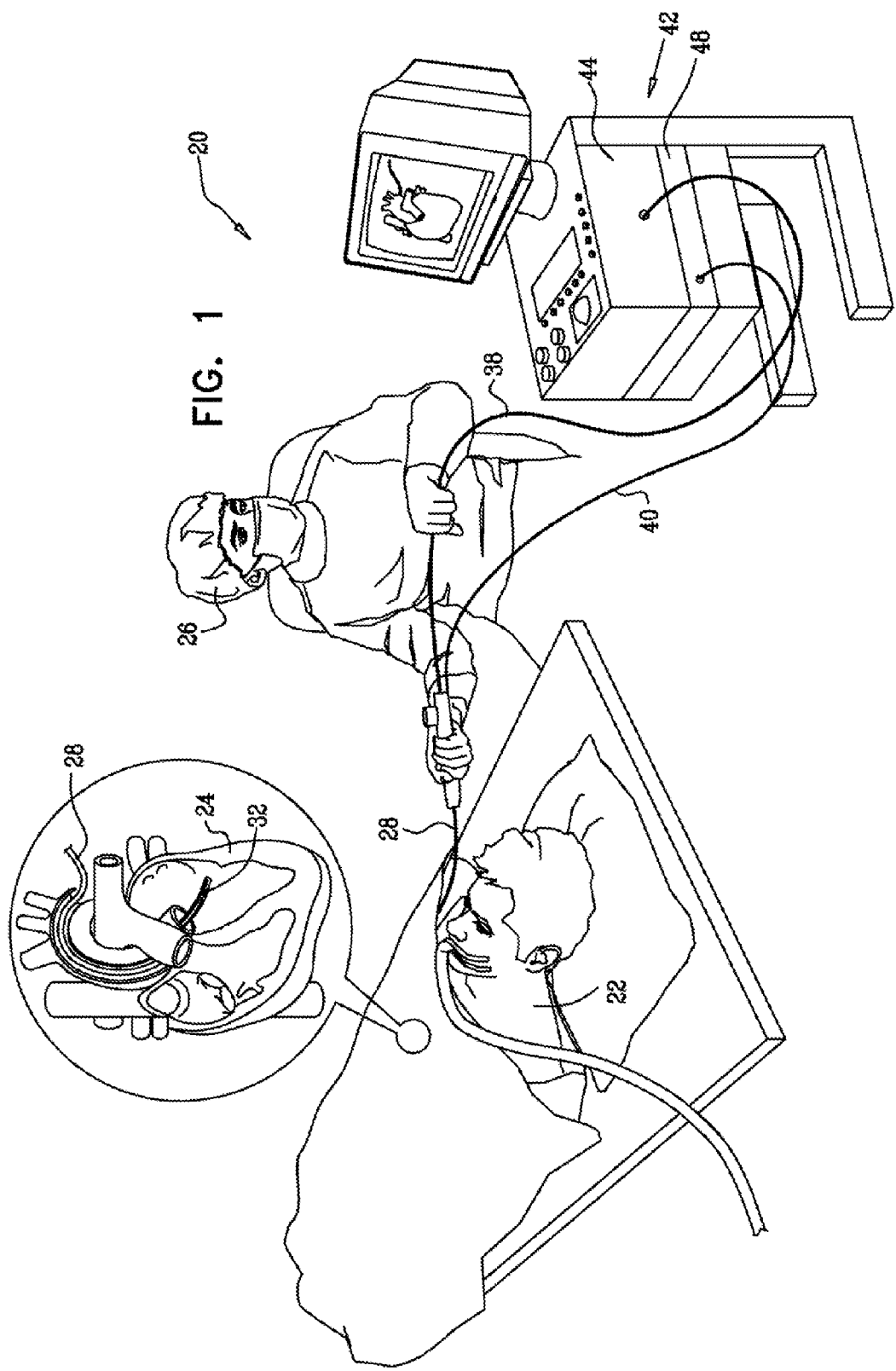
FIG. 1 is a schematic, pictorial illustration of a system for cardiac ablation therapy, in accordance with an embodiment of the present invention.

FIG. 1 is a schematic, pictorial illustration of a system 20 for cardiac ablation therapy, in accordance with an embodiment of the present invention. An operator 26 inserts a catheter 28 through a blood vessel into a chamber of a heart 24 of a subject 22, and manipulates the catheter so that a distal portion 32 of the catheter contacts the endocardium in an area that is to be treated. The distal portion of the catheter is perforated to enable irrigation of the treatment area, as shown and described hereinbelow. In other respects, however, system 20 resembles systems for cardiac ablation treatment that are known in the art, such as the above-mentioned Biosense Webster system, and the components of such systems may be adapted for use in system 20.

After positioning distal portion 32 of catheter 28 at an ablation site, and ensuring that an electrode on the distal portion (as shown below) is in contact with the endocardium at the site, operator 26 actuates a radio frequency (RF) energy generator 44 in a control console 42 to supply RF energy via a cable 38 to the electrode. Meanwhile, an irrigation pump 48 supplies a cooling fluid, such as saline solution, via a tube 40 and a lumen in catheter 28 to the distal portion. Operation of the RF energy generator and the irrigation pump may be coordinated in order to give the appropriate volume of irrigation during ablation, so as to cool the electrode and the tissue without overloading the heart with irrigation fluid. A temperature sensor (not shown in the figures) in distal portion 32 may provide feedback to console 42 for use in controlling the RF energy dosage and/or irrigation volume.

Figure 2:
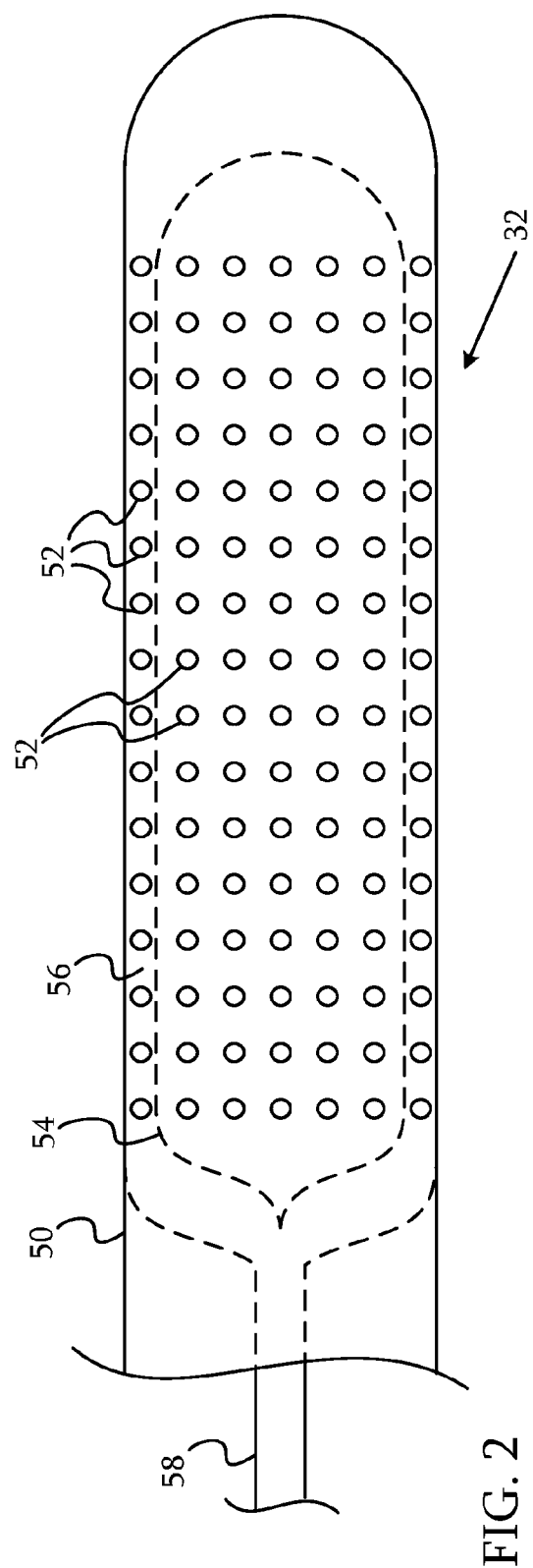
FIG. 2 is a schematic side view of a perforated catheter insertion tube, in accordance with an embodiment of the present invention.

FIG. 2 is a schematic side view of a portion of an insertion tube 50 of catheter 28, in accordance with an embodiment of the present invention. The figure shows the distal portion of the insertion tube at a stage of manufacturing before assembly of an electrode onto distal portion 32. Tube 50 typically comprises a suitable biocompatible plastic, such as polyurethane, which is typically about 2.3 mm in diameter, with a wall thickness of about 0.15 mm. These dimensions, however, are given solely by way of illustration, and larger or smaller dimensions may be used depending on application requirements.

The outer surface of the distal portion of tube 50 is penetrated by multiple perforations 52, which are distributed over the surface of the distal tip both longitudinally (i.e., along the direction parallel to the longitudinal axis of catheter 28) and circumferentially (along circumferences around the axis). The perforations may be formed in tube 50 by any suitable method known in the art, such as pre-molding of the perforations at the time of fabrication of the tube, or punching or drilling (by laser or mechanical means) the perforations into the tube after extrusion.

Distal portion 32 contains an interior reservoir 56, which is fed with irrigation fluid by a lumen 58 inside tube 50. Perforations 52 extend between reservoir 56 and the outer surface of tube 50. In the embodiment shown in the figures, reservoir 56 has an inner surface 54, which may be formed, for example, by a fitting a tube of smaller diameter inside tube 50. Alternatively, the reservoir may occupy the entire interior space at the distal tip of tube 50, which may then be closed off by a plug (not shown) proximal to the distal tip, through which lumen 58 feeds. Alternative reservoir configurations will be apparent to those skilled in the art and are considered to be within the scope of the present invention.

Typically, tube 50 has at least eight perforations, which are less than 0.5 mm in diameter, in order to distribute the irrigation over the area of distal portion both longitudinally and circumferentially without overloading the heart with the cooling fluid. The inventors have found it advantageous, however, to have at least fifty perforations in the distal portion, with diameters no greater than 0.2 mm, and possibly as small as about 0.1 mm. The sizes of the perforations may optionally be varied over the length of the distal tip to compensate for pressure variation and ensure equal flow over the entire length. For this purpose, the perforations at and near the most distal part of the tip may be made larger than the more proximal perforations, which are nearer to the fluid inlet.

Figure 3:
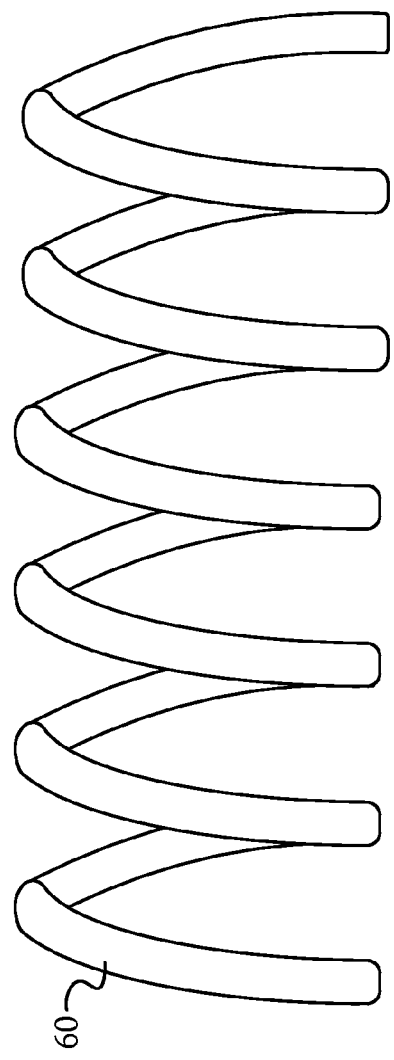
FIG. 3 is a schematic side view of a coil electrode, in accordance with an embodiment of the present invention.

FIG. 3 is a schematic side view of a coil electrode 60, in accordance with an embodiment of the present invention. This electrode is fitted over tube 50, as shown in the figures that follow. Electrode 60 typically comprises a resilient, biocompatible conductive material, such as gold, platinum or iridium wire, or an alloy of such metals. The coil electrode may comprise a wire, which is wound into a helical coil, as shown in the figure, resembling a coil spring. Alternatively, the coil electrode may be made from a tube, which is cut out along a spiral pattern to create a helical shape, using laser cutting, for example. The coil electrode has an inner diameter equal to or slightly smaller than the outer diameter of tube 50, so that the coil will fit snugly over the tube.

Reference is now made to FIGS. 4 and 5, which schematically show distal portion 32 of catheter 28, made by fitting coil electrode 60 over tube 50, in accordance with an embodiment of the present invention. FIG. 4 is a side view, while FIG. 5 is a cross-sectional view taken along the line marked V-V in FIG. 4. Electrode 60 is slid to the desired location on tube 50, and is then glued or otherwise fastened in place. One or more wires 62 inside tube 50 penetrate through the outer surface of the tube (possibly through one of perforations 52) and are soldered or otherwise bonded to electrode 60. Any suitable technique that is known in the art for electrical coupling to ring electrodes may similarly be used for this purpose. Wires 62 run through to the proximal end of catheter 28, where they connect via cable 38 to RF energy generator 44 (FIG. 1).

As can be seen in FIGS. 4 and 5, when electrode 60 is fastened over tube 50, it covers some of the perforations (marked 52B in FIG. 5). A sufficient number of the perforations (marked 52A) remain open, however, to provide adequate irrigation of the area contacted by the electrode. This arrangement is advantageous in that it obviates the need for high positional precision in forming perforations 52 in tube 50 and in placing electrode 60 on the tube. During the ablation procedure, lumen 58 (FIG. 2) conveys fluid from irrigation pump 48 (FIG. 1) to reservoir 56. The fluid exits tube 50 through perforations 52A to the surrounding tissue while electrode 60 delivers the RF energy in order to ablate the tissue.

Figure 6:
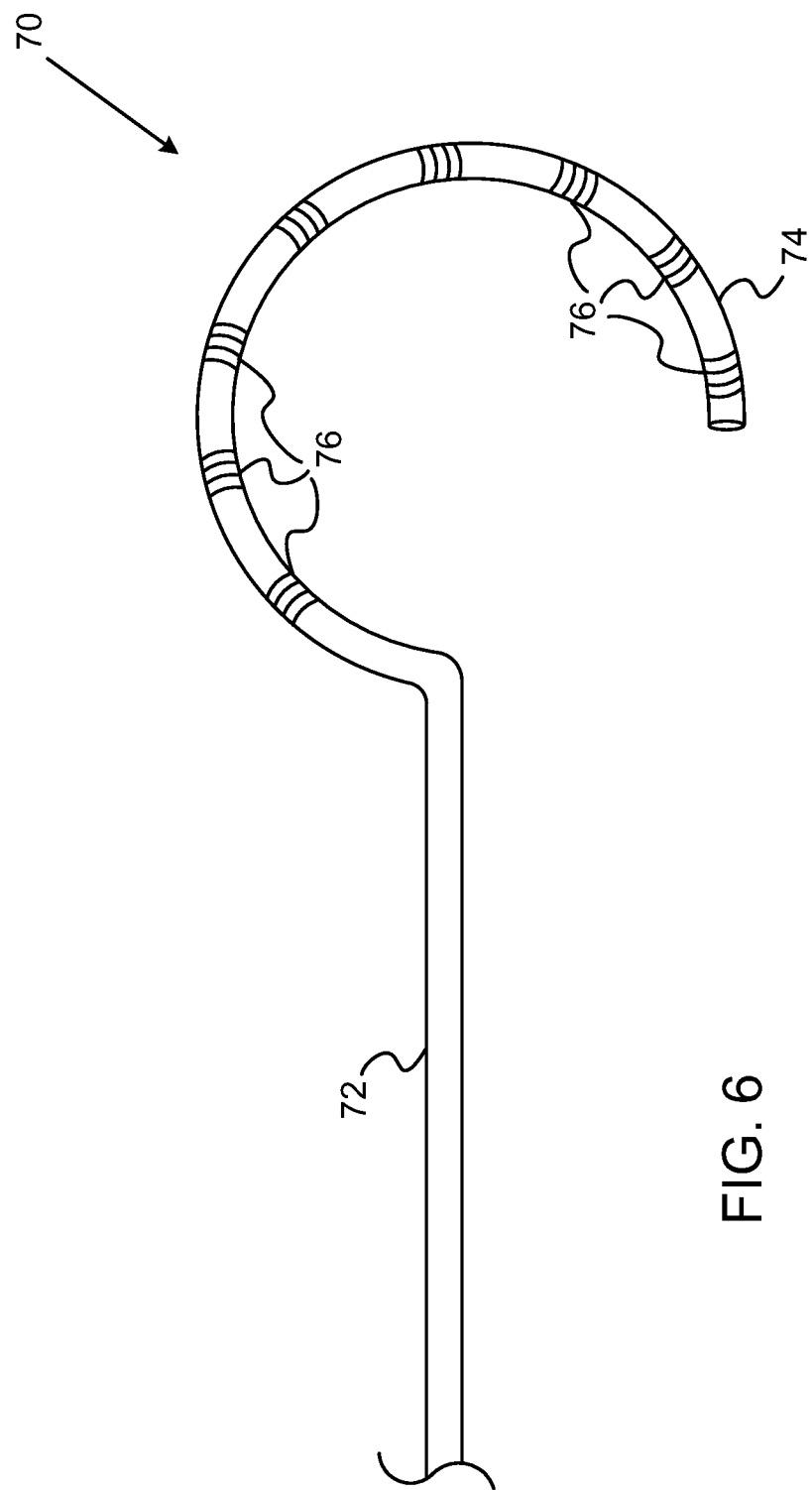
FIG. 6 is a schematic side view of a lasso catheter with coil electrodes, in accordance with an embodiment of the present invention.

FIG. 6 is a schematic side view of a lasso catheter with coil electrodes 76, in accordance with an embodiment of the present invention. The lasso catheter insertion tube is formed to define a shaft 72 with a distal portion 74 having a roughly circular lasso shape. This sort of lasso shape can be used, for example, in ablating myocardial tissue along a circular path around the ostia of the pulmonary veins in treatment of atrial fibrillation.

In order to ablate multiple locations simultaneously along the desired path, electrodes 76 are distributed around the circumference of distal portion 74. Each electrode is slid into place, fastened, and connected electrically to wires inside catheter 70 in the manner described above. Distal portion 74 may also have perforations (not shown in this figure) for the purpose of irrigation, as in catheter 28. Multiple coil electrodes may likewise be distributed along the length of catheters of other types, as well as on other sorts of tubular probes.

Although the embodiments described above relate specifically to catheters used in RF ablation treatment within the heart, the principles of the present invention may similarly be applied to other organs and in other types of diagnostic and therapeutic procedures, particularly procedures that involve application of energy to body tissues. For example, a device with a similar sort of irrigated tip may be used in therapies that involve microwave-based or ultrasonic tissue heating. As another example, coil electrodes of the type described above may also be used without irrigation on catheters and tubular probes of other types.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for producing a medical device, comprising:
    creating a plurality of perforations through an outer surface of a distal portion of an insertion tube containing a lumen and having an outer diameter, so as to provide fluid communication between the lumen and an outer surface of the insertion tube;
    cutting a metal tube into a spiral pattern to form at least one helical electrode, the helical electrode having an inner diameter slightly smaller than the outer diameter of the insertion tube; and
    after cutting the metal tube to form the at least one helical electrode, sliding said formed at least one helical electrode over the distal portion of the insertion tube; and
    affixing the at least one helical electrode to the outer surface of the distal portion of the insertion tube.

2. The method according to claim 1, and comprising passing one or more wires through the tube and electrically coupling the wires to the at least one helical electrode.

3. The method according to claim 1, wherein the at least one helical electrode covers some, but not all, of the perforations.

4. The method according to claim 1, wherein sliding the at least one helical electrode comprises positioning multiple helical electrodes along the distal portion.

5. A method for producing a medical device, comprising:
    creating a plurality of perforations through an outer surface of a distal portion of an insertion tube containing a lumen so as to provide fluid communication between the lumen and an outer surface of the insertion tube;
    winding a metal wire into a helical coil to form a helical electrode, the helical electrode having an inner diameter slightly smaller than the outer diameter of the insertion tube; and
    after the step of winding, sliding said at least one helical electrode over the distal portion of the insertion tube; and
    affixing the at least one helical electrode to the outer surface of the distal portion of the insertion tube.

6. The method according to claim 5, and comprising passing one or more wires through the tube and electrically coupling the wires to the at least one helical electrode.

7. The method according to claim 5, wherein the at least one helical electrode covers some, but not all, of the perforations.

8. The method according to claim 5, wherein sliding the at least one helical electrode comprises positioning multiple helical electrodes along the distal portion.

9. The method according to claim 1 or 5, wherein the size of the perforations are varied over the length of the distal portion to compensate for pressure variation and flow over the length of distal portion.

10. The method according to claim 1 or 5, wherein the perforations are sized and configured to ensure near equal flow of the entire length of the distal portion.

* * * * *